US010371687B2

(12) United States Patent
Nakasaka

(10) Patent No.: US 10,371,687 B2
(45) Date of Patent: Aug. 6, 2019

(54) AIR-FUEL RATIO DETECTION DEVICE FOR INTERNAL COMBUSTION ENGINE

(71) Applicant: TOYOTA JIDOSHA KABUSHIKI KAISHA, Toyota-shi, Aichi-ken (JP)

(72) Inventor: Yukihiro Nakasaka, Shizuoka-ken (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 218 days.

(21) Appl. No.: 15/123,737

(22) PCT Filed: Jan. 14, 2015

(86) PCT No.: PCT/JP2015/050830
§ 371 (c)(1),
(2) Date: Sep. 6, 2016

(87) PCT Pub. No.: WO2015/133172
PCT Pub. Date: Sep. 11, 2015

(65) Prior Publication Data
US 2017/0016872 A1    Jan. 19, 2017

(30) Foreign Application Priority Data

Mar. 7, 2014    (JP) .................................. 2014-045529

(51) Int. Cl.
F02D 41/00    (2006.01)
F02D 41/14    (2006.01)
(Continued)

(52) U.S. Cl.
CPC ......... G01N 33/22 (2013.01); F02D 41/0085 (2013.01); F02D 41/1458 (2013.01);
(Continued)

(58) Field of Classification Search
CPC .............. F02D 35/023; F02D 41/1454; F02D 41/1497; F02D 41/0085; F02D 41/1458; G01N 33/22; G01L 21/26; G01M 15/08
(Continued)

(56) References Cited

U.S. PATENT DOCUMENTS

2009/0299612 A1* 12/2009 Truscott ................ F02D 35/023
701/108
2013/0073189 A1*  3/2013 Korenaga ........... F02D 41/1497
701/111
2015/0192083 A1*  7/2015 Suzuki ................ F02D 41/1454
701/101

FOREIGN PATENT DOCUMENTS

JP    H03-23349 A    1/1991
JP    2005-133604 A   5/2005
(Continued)

Primary Examiner — Regis J Betsch
Assistant Examiner — Kaleria Knox
(74) Attorney, Agent, or Firm — Hunton Andrews Kurth LLP

(57) ABSTRACT

An in-cylinder pressure sensor is provided. It is determined whether a cylinder for which the in-cylinder air-fuel ratio is to be calculated is a rich cylinder or a lean cylinder. A polytropic index in the expansion stroke is calculated from the in-cylinder pressure detected by the in-cylinder pressure sensor. The calculated polytropic index m is corrected based on an operational condition parameter of an internal combustion engine. An in-cylinder air-fuel ratio is calculated based on the corrected polytropic index m in the expansion stroke, the result of the determination of whether the cylinder is a rich cylinder or a lean cylinder, and an m-A/F curve.

8 Claims, 7 Drawing Sheets

(51) Int. Cl.
*G01L 23/26* (2006.01)
*G01M 15/08* (2006.01)
*G01N 33/22* (2006.01)

(52) U.S. Cl.
CPC ............ *G01L 23/26* (2013.01); *G01M 15/08* (2013.01); *F02D 2200/0402* (2013.01); *F02D 2200/0406* (2013.01)

(58) Field of Classification Search
USPC .................................................. 701/101, 108
See application file for complete search history.

(56) References Cited

FOREIGN PATENT DOCUMENTS

| | | | |
|---|---|---|---|
| JP | 2010-007581 | A | 1/2010 |
| JP | 2010-133353 | A | 6/2010 |
| JP | 2011-111906 | A | 6/2011 |
| JP | 2012-180817 | A | 9/2012 |
| JP | 2013-142302 | A | 7/2013 |

* cited by examiner

[Fig. 1]
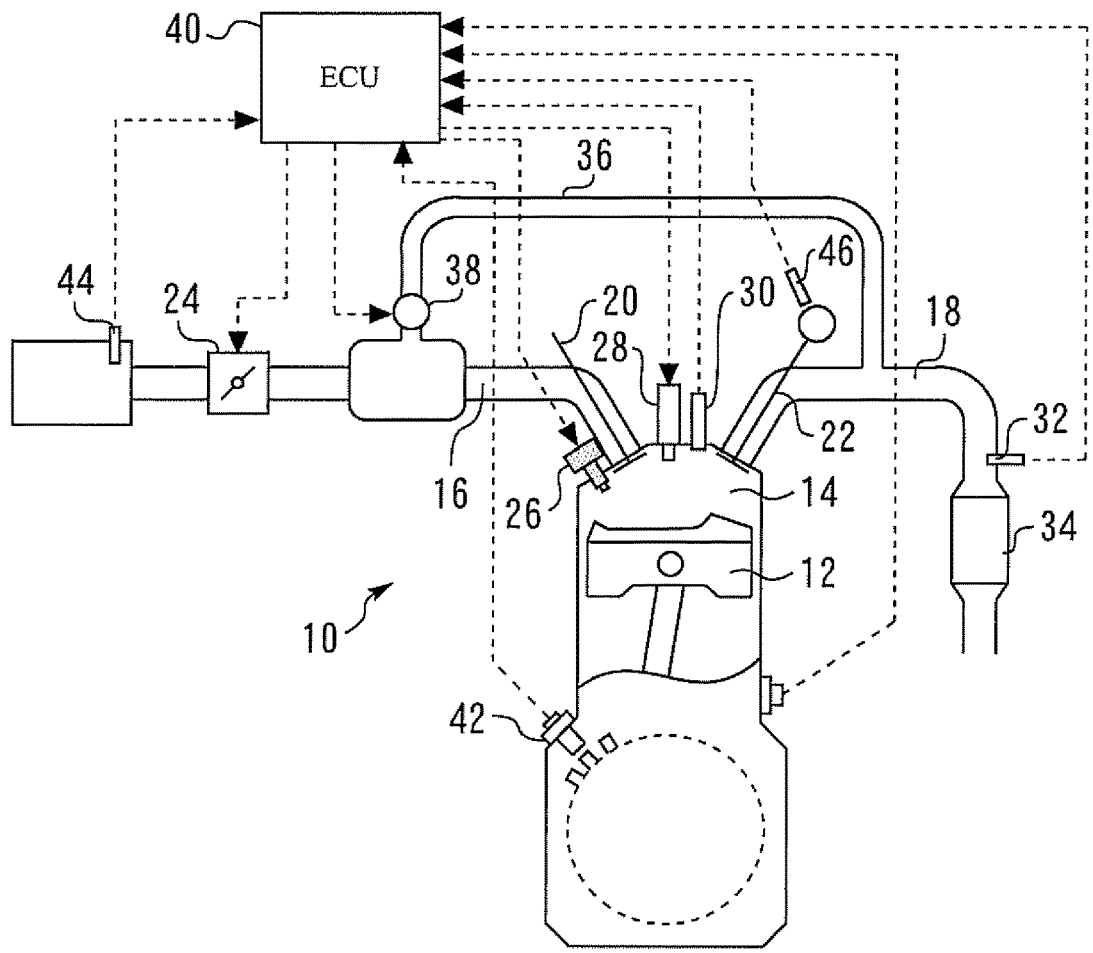
[Fig. 2]
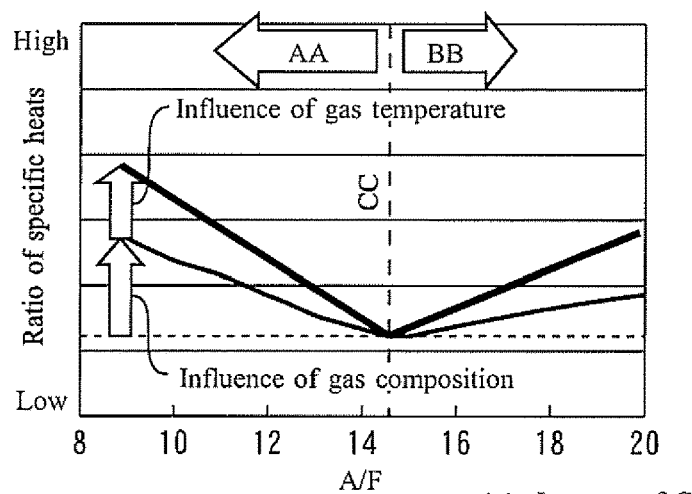
AA: Increase of CO, H2
BB: Increase of O2
CC: Stoichiometric air-fuel ratio

[Fig. 3]
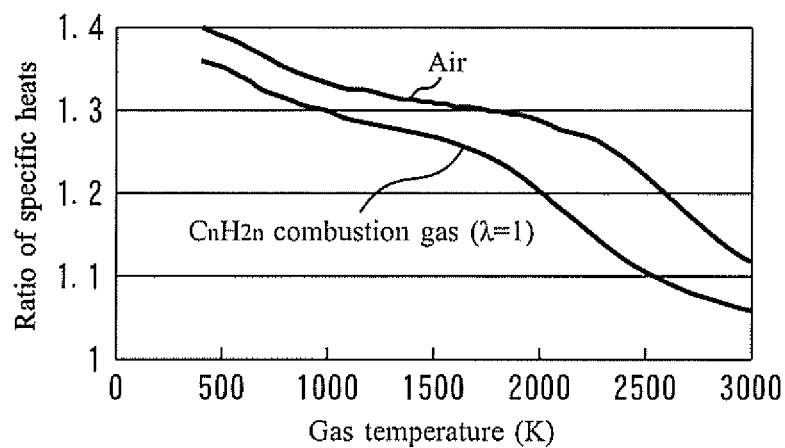
[Fig. 4]
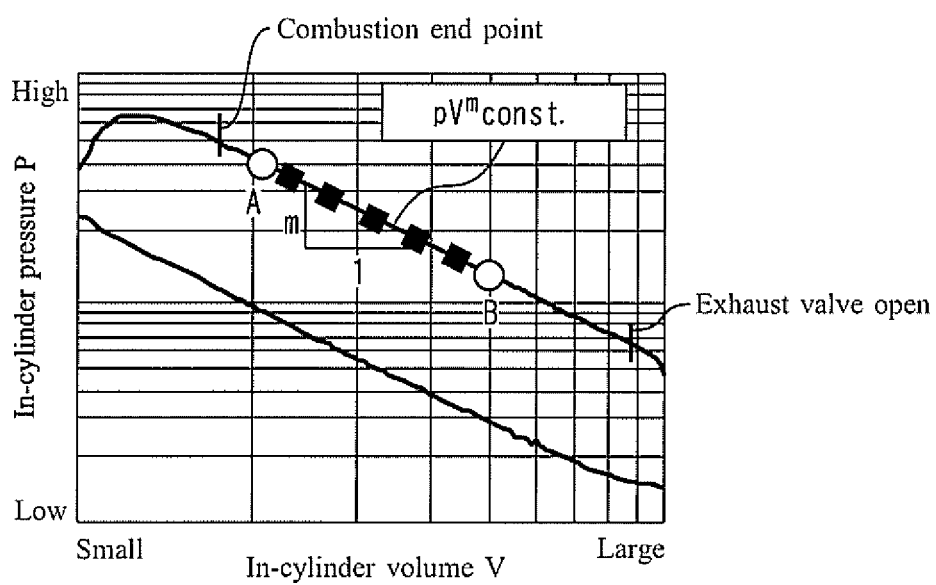

[Fig. 5A]
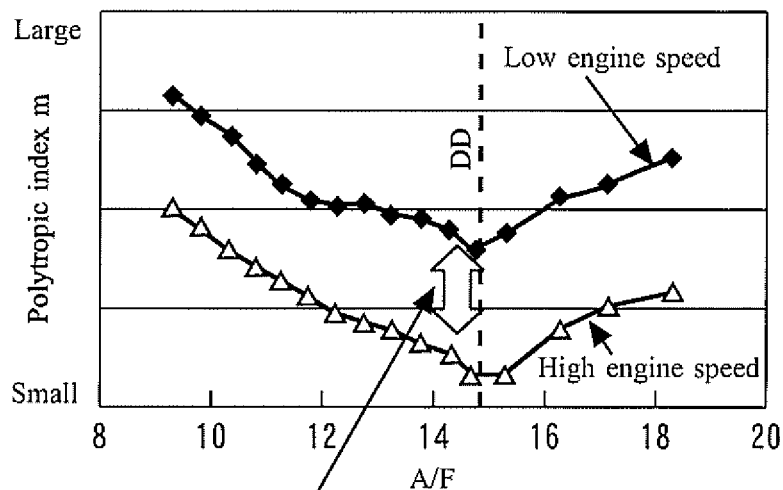
[Fig. 5B]
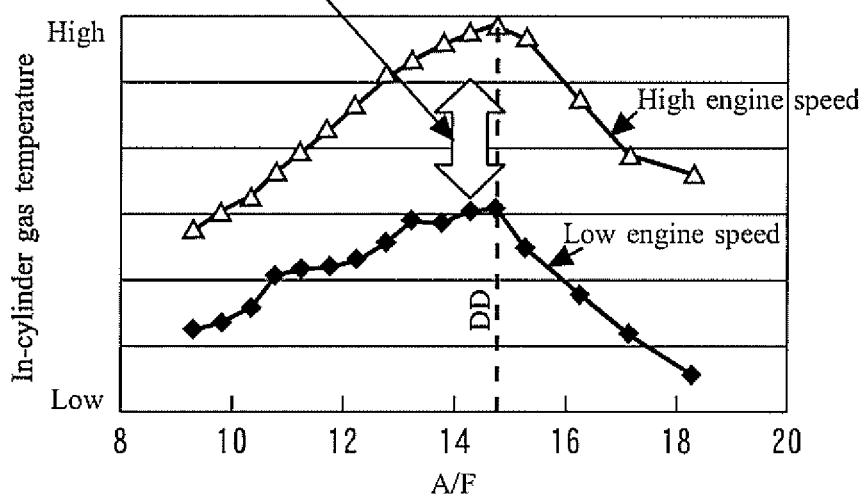
DD: Stoichiometric air-fuel ratio
EE: Equivalent to difference in ratio of specific heats according to diffrerence in gas temperature

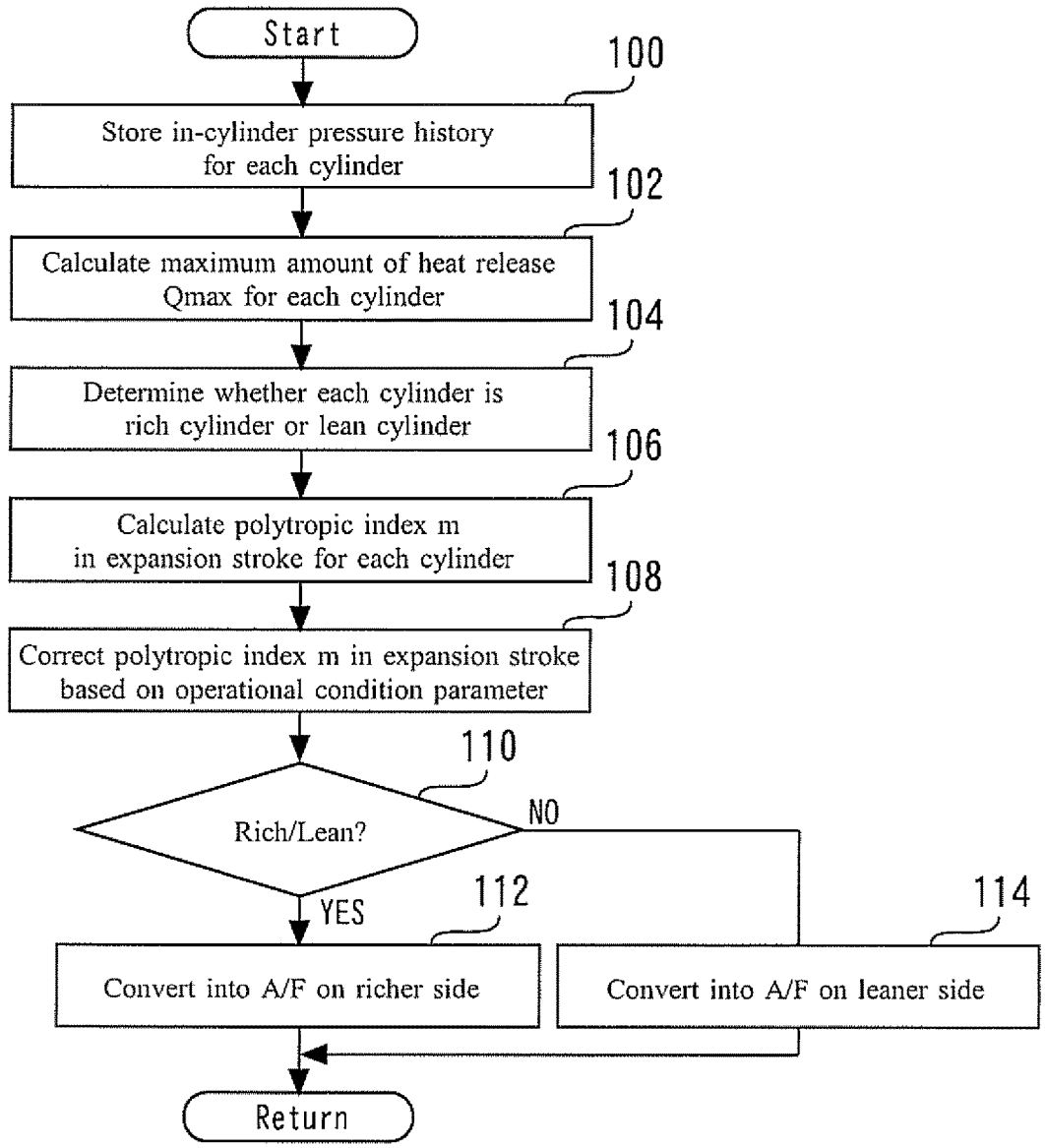
[Fig. 6]

[Fig. 7A]
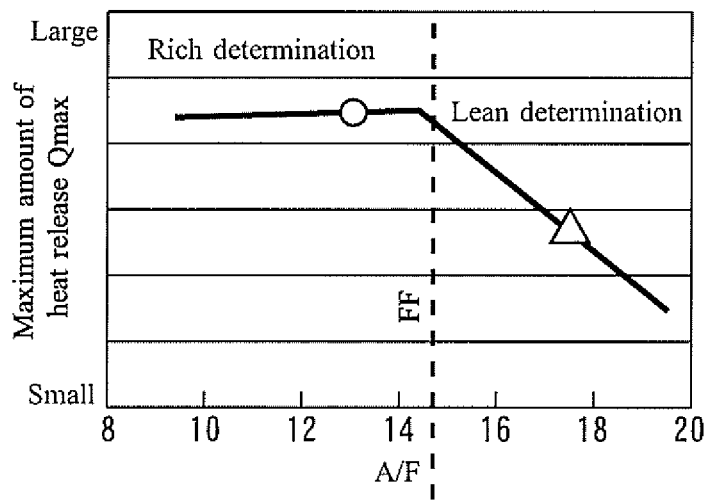
[Fig. 7B]
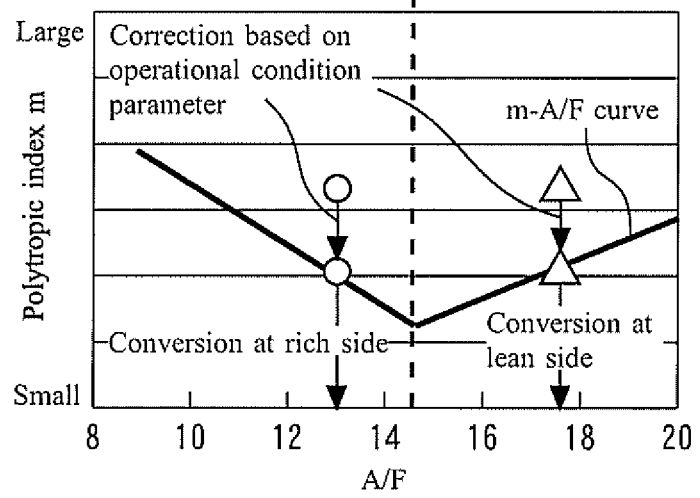
FF: Stoichiometric air-fuel ratio

[Fig. 8A]
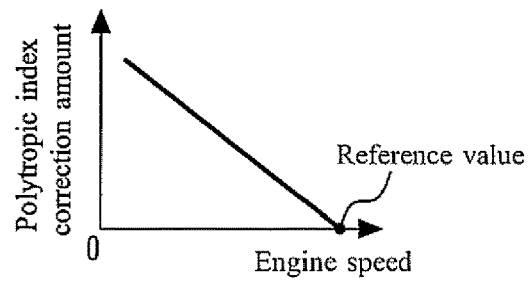
[Fig. 8B]
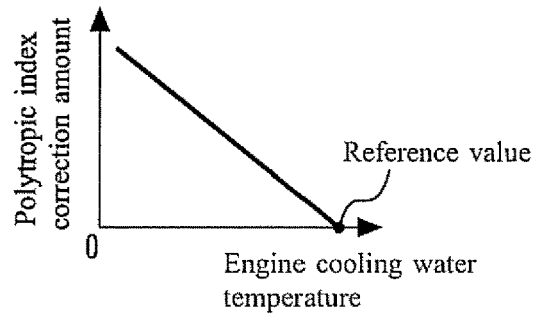
[Fig. 8C]
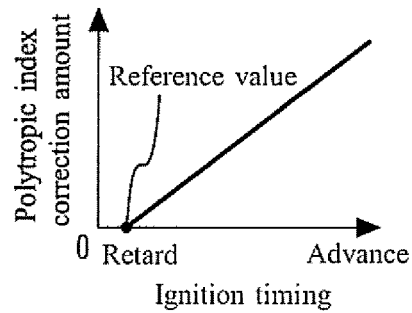
[Fig. 8D]
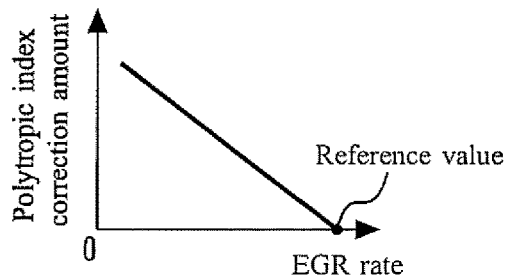
[Fig. 8E]
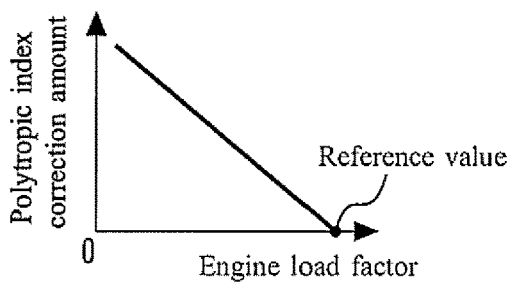

[Fig. 9]
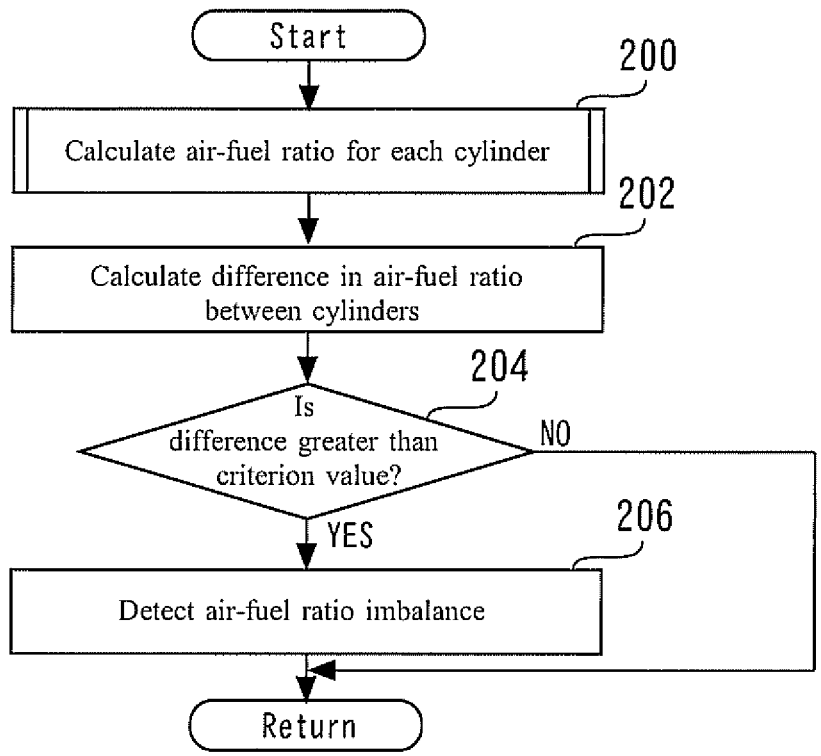
[Fig. 10]
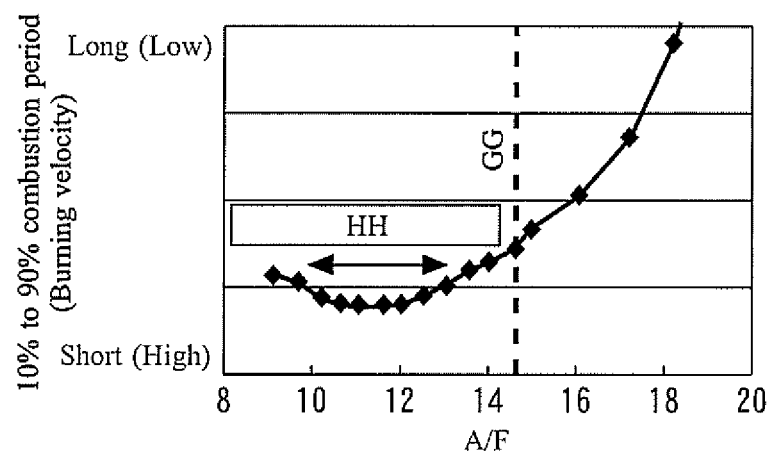
GG: Stoichiometric air-fuel ratio
HH: Less sensitive in rich region

AIR-FUEL RATIO DETECTION DEVICE FOR INTERNAL COMBUSTION ENGINE

CROSS-REFERENCE TO RELATED APPLICATIONS

This is a national phase application based on the PCT International Patent Application No. PCT/JP2015/050830 filed Jan. 14, 2015, claiming priority to Japanese Patent Application No. 2014-045529 filed Mar. 7, 2014, the entire contents of both of which are incorporated herein by reference.

TECHNICAL FIELD

The present invention relates to an air-fuel ratio detection device for an internal combustion engine.

BACKGROUND

For example, PTL1 discloses an air-fuel ratio detection device for an internal combustion engine that uses an in-cylinder pressure sensor to detect the air-fuel ratio or an air-fuel ratio imbalance between cylinders. The air-fuel ratio detection device changes the fuel injection amount for a target cylinder so that the burning velocity reaches a peak value. Information on the air-fuel ratio of the target cylinder is calculated based on the change of the fuel injection amount between the time when the fuel injection amount starts being changed and the time when the peak value of the burning velocity is reached.

CITATION LIST

Patent Literature

[PTL 1] JP2013-142302A
[PTL 2] JP03-023349A
[PTL 3] JP2010-133353A
[PTL 4] JP2012-180817A
[PTL 5] JP2005-133604A
[PTL 6] JP2010-007581A
[PTL 7] JP2011-111906A

SUMMARY OF INVENTION

Technical Problem

As a combustion parameter correlated to the air-fuel ratio of the in-cylinder gas, an amount of in-cylinder heat release or a burning velocity of the combustion can be calculated from an output value of an in-cylinder pressure sensor, for example. The amount of heat release and the burning velocity are both highly sensitive to the air-fuel ratio in a region leaner than the stoichiometric air-fuel ratio. However, in a region richer than the stoichiometric air-fuel ratio, the amount of heat release and the burning velocity are less sensitive to the air-fuel ratio, and it is difficult to accurately determine the air-fuel ratio from the amount of heat release or the burning velocity.

The present invention has been devised to address the problem described above, and an object of the present invention is to provide an air-fuel ratio detection device for an internal combustion engine that can calculate, using in-cylinder pressure detecting means, an index value of an in-cylinder air-fuel ratio including the index value in a region where the air-fuel ratio is richer than the stoichiometric air-fuel ratio.

Solution to Problem

A first aspect of the present invention is an air-fuel ratio detection device for an internal combustion engine that includes: in-cylinder pressure detecting means for detecting an in-cylinder pressure; cylinder air-fuel ratio determining means for determining whether a cylinder for which an index value of an in-cylinder air-fuel ratio is to be calculated is a rich cylinder, for which the in-cylinder air-fuel ratio is richer than a stoichiometric air-fuel ratio, or a lean cylinder, for which the in-cylinder air-fuel ratio is leaner than the stoichiometric air-fuel ratio; and polytropic index calculating means for calculating a polytropic index in an expansion stroke from the in-cylinder pressure detected by the in-cylinder pressure detecting means. The polytropic index calculating means corrects the calculated polytropic index based on an operational condition parameter of the internal combustion engine. The air-fuel ratio detection device further includes air-fuel ratio calculating means for calculating the index value of the in-cylinder air-fuel ratio based on the corrected polytropic index in the expansion stroke, a result of the determination of whether the cylinder for which the index value of the in-cylinder air-fuel ratio is to be calculated is a rich cylinder or a lean cylinder, and relationship information that prescribes a relationship between the polytropic index in the expansion stroke and the index value of the in-cylinder air-fuel ratio under a reference operational condition.

A second aspect of the present invention is the air-fuel ratio detection device for an internal combustion engine according to the first aspect of the present invention, wherein the operational condition parameter used for the correction of the polytropic index in the expansion stroke is at least one of an engine speed, a temperature of engine cooling water, an ignition timing, an EGR rate and an engine load factor.

A third aspect of the present invention is the air-fuel ratio detection device for an internal combustion engine according to the first or second aspect of the present invention, wherein the polytropic index calculating means corrects the polytropic index in the expansion stroke so as to be smaller as the engine speed is higher, as the temperature of the engine cooling water is higher, as the ignition timing is retarded, as the EGR rate is higher, or as the engine load factor is higher.

A fourth aspect of the present invention is the air-fuel ratio detection device for an internal combustion engine according to any one of the first to third aspects of the present invention, wherein the cylinder air-fuel ratio determining means calculates an amount of heat release or a burning velocity from the in-cylinder pressure detected by the in-cylinder pressure detecting means and determines that the cylinder for which the index value of the in-cylinder air-fuel ratio is to be calculated is a rich cylinder when the calculated amount of heat release or burning velocity is greater than a predetermined value.

A fifth aspect of the present invention is the air-fuel ratio detection device for an internal combustion engine according to any one of the first to fourth aspects of the present invention, wherein the polytropic index calculating means calculates the polytropic index in the expansion stroke from in-cylinder pressures and in-cylinder volumes at two or more points in the expansion stroke at or after a combustion end point and before an opening timing of an exhaust valve.

A sixth aspect of the present invention is the air-fuel ratio detection device for an internal combustion engine according to any one of the first to fifth aspects of the present invention, wherein the internal combustion engine includes a plurality of cylinders, wherein the in-cylinder pressure detecting means detects an in-cylinder pressure of each of the plurality of cylinders, and wherein the air-fuel ratio detection device further includes imbalance detecting means for determining that the air-fuel ratio is imbalance between cylinders when a difference in air-fuel ratio between the cylinders based on the index value of the in-cylinder air-fuel ratio calculated by the air-fuel ratio calculating means is greater than a predetermined criterion value.

A seventh aspect of the present invention is the air-fuel ratio detection device for an internal combustion engine according to any one of the first to sixth aspects of the present invention, wherein the reference operational condition is an operational condition where the operational condition parameter equals an arbitrary reference value.

An eighth aspect of the present invention is the air-fuel ratio detection device for an internal combustion engine according to any one of the first to seventh aspects of the present invention, wherein the relationship information is a curve that prescribes a relationship between the polytropic index in the expansion stroke and the index value of the in-cylinder air-fuel ratio in an X-Y plane with an X axis indicating the index value of the in-cylinder air-fuel ratio and a Y axis indicating the polytropic index in the expansion stroke.

Advantageous Effects of Invention

There is a correlation between the polytropic index in the expansion stroke and the index value of the in-cylinder air-fuel ratio. However, each of the ratio of specific heats and the polytropic index m is not uniquely determined by the relationship with the in-cylinder air-fuel ratio. This is because each of the ratio of specific heats and the polytropic index is affected by the temperature of the gas in the cylinder, which changes with the cooling loss, which changes with the value of an operational condition parameter of the internal combustion engine, such as the engine speed or the temperature of the engine cooling water. In addition, the relationship between the polytropic index in the expansion stroke and the index value of the air-fuel ratio has a tendency of the polytropic index to be lowest at the stoichiometric air-fuel ratio and increase as the air-fuel ratio becomes richer or leaner than the stoichiometric air-fuel ratio. Thus, the same polytropic index can be attained at different values of the index value of the air-fuel ratio. According to the first, seventh and eighth aspects of the present invention, it is determined whether the cylinder for which the index value of the in-cylinder air-fuel ratio is to be calculated is a rich cylinder, for which the in-cylinder air-fuel ratio is richer than the stoichiometric air-fuel ratio, or a lean cylinder, for which the in-cylinder air-fuel ratio is leaner than the stoichiometric air-fuel ratio. In addition, the polytropic index in the expansion stroke calculated from the in-cylinder pressure is corrected based on the operational condition parameter of the internal combustion engine. Furthermore, the index value of the in-cylinder air-fuel ratio is calculated based on the corrected polytropic index in the expansion stroke, the result of the determination of whether the cylinder for which the index value of the in-cylinder air-fuel ratio is to be calculated is a rich cylinder or a lean cylinder, and the relationship information that prescribes a relationship between the polytropic index in the expansion stroke and the index value of the in-cylinder air-fuel ratio under the reference operational condition. Thus, the index value of the in-cylinder air-fuel ratio including the index value in a region where the air-fuel ratio is richer than the stoichiometric air-fuel ratio can be calculated from the polytropic index in the expansion stroke calculated from the in-cylinder pressure detected by the in-cylinder pressure detecting means.

According to the second and third aspect of the present invention, the change of the polytropic index due to the change of the value of the operational condition parameter can be appropriately corrected.

According to the fourth aspect of the present invention, it can be appropriately determined from the in-cylinder pressure detected by the in-cylinder pressure detecting means that the cylinder for which the index value of the in-cylinder air-fuel ratio is to be calculated is a rich cylinder.

According to the fifth aspect of the present invention, the polytropic index in the expansion stroke can be appropriately calculated.

According to the sixth aspect of the present invention, an air-fuel ratio imbalance between cylinders can be appropriately detected from the polytropic index in the expansion stroke that is based on the in-cylinder pressure detected by the in-cylinder pressure detecting means.

BRIEF DESCRIPTION OF DRAWINGS

FIG. 1 is a diagram for illustrating a system configuration of an internal combustion engine according to a first embodiment of the present invention;

FIG. 2 is a graph showing a relationship between the ratio ($\kappa$) of specific heats of a burned gas and the air-fuel ratio (A/F) noted in the first embodiment of the present invention;

FIG. 3 is a graph showing a relationship between the ratio of specific heats and the gas temperature;

FIG. 4 is a log-log P-V graph for the compression stroke and the expansion stroke of the internal combustion engine;

FIG. 5A and FIG. 5B are graphs for illustrating a relationship between the change of the temperature of the gas in the cylinder and the change of the polytropic index m in the expansion stroke;

FIG. 6 is a flowchart showing a routine performed to implement a method of detecting the air-fuel ratio in each cylinder according to the first embodiment of the present invention;

FIG. 7A and FIG. 7B are graphs for illustrating a specific example of the method of detecting the air-fuel ratio according to the first embodiment of the present invention;

FIG. 8A to FIG. 8E are graphs showing settings of various polytropic index correction amounts used in the processing of Step 108 in FIG. 6;

FIG. 9 is a flowchart showing a routine performed to implement a process of detecting an air-fuel ratio imbalance between cylinders; and FIG. 10 is a graph showing a relationship between the burning velocity and the in-cylinder air-fuel ratio.

DESCRIPTION OF EMBODIMENTS

First Embodiment
[System Configuration According to First Embodiment]

FIG. 1 is a diagram for illustrating a system configuration of an internal combustion engine 10 according to a first embodiment of the present invention. The system shown in FIG. 1 includes a multi-cylinder internal combustion engine 10. In this example, the internal combustion engine 10 is an in-line four cylinder gasoline engine of the spark ignition type. A piston 12 is provided in each cylinder of the internal combustion engine 10. A combustion chamber 14 is formed in the cylinder at the top side of the piston 12. The combustion chamber 14 is in communication with an intake channel 16 and an exhaust channel 18.

An intake valve 20 that opens and closes an intake port of the intake channel 16 is provided for the intake port, and an exhaust valve 22 that opens and closes an exhaust port of the exhaust channel 18 is provided for the exhaust port. Furthermore, an electronically controlled throttle valve 24 is provided in the intake channel 16.

Each cylinder of the internal combustion engine 10 is provided with a fuel injection valve 26 that is used to directly inject a fuel into the combustion chamber 14 (into the cylinder) and an ignition device having a spark plug 28 that ignites an air-fuel mixture. Furthermore, each cylinder incorporates an in-cylinder pressure sensor 30 that detects an in-cylinder pressure. An air-fuel ratio sensor 32 that detects the air-fuel ratio of an exhaust gas is attached to the exhaust channel 18 at a part downstream of the confluence of the exhaust gas from the cylinders. As an exhaust gas purifying catalyst that purifies the exhaust gas, a three way catalyst 34 is disposed in the exhaust channel 18 downstream of the air-fuel ratio sensor 32.

The internal combustion engine 10 is further provided with an EGR channel 36 that connects the exhaust channel 18 and the intake channel 16 to each other. The EGR channel 36 is provided with an EGR valve 38 that adjusts the amount of the exhaust gas (EGR gas) flown back into the intake channel 16. An EGR rate can be adjusted by adjusting the opening of the EGR valve 38.

The system according to this embodiment further includes an electronic control unit (ECU) 40. Various sensors from which the ECU 40 obtains information on the operational state of the internal combustion engine 10, such as the in-cylinder pressure sensor 30 described above, a crank angle sensor 42 that detects the crank angle and the engine speed, an air flow sensor 44 that detects the intake air amount and an exhaust cam angle sensor 46 that detects the rotational angle of an exhaust cam shaft (not shown) that drives the exhaust valve 22, are connected to an input part of the ECU 40. The exhaust cam angle sensor 46 can detect the timing of opening and closing of the exhaust valve 22, which is adjusted by an exhaust variable valve timing device (not shown) that can change the timing of opening and closing of the exhaust valve 22. Various actuators that control operation of the internal combustion engine 10, such as the throttle valve 24, the fuel injection valve 26, the ignition device and the EGR valve 38 described above, are connected to an output part of the ECU 40. The ECU 40 has a function of obtaining an output signal of the in-cylinder pressure sensor 30 A/D-converted in synchronization with the crank angle. Thus, the ECU 40 can detect the in-cylinder pressure at an arbitrary crank angle position within the range that allowed by the resolution of the A/D conversion. Furthermore, the ECU 40 has a function of calculating the value of the in-cylinder volume, which is determined by the crank angle position, in accordance with the crank angle. The ECU 40 performs predetermined engine controls, such as fuel injection control and ignition control, by driving the various actuators described above based on the outputs of the various sensors according to predetermined programs. As one of such engine controls, the ECU 40 performs an air-fuel ratio feedback control, which is to adjust the fuel injection amount for each cylinder so as to set the air-fuel ratio of the exhaust gas flowing to the three way catalyst 34 (that is, the confluent exhaust gas of the exhaust gas from the cylinders) at the stoichiometric air-fuel ratio when a predetermined execution condition is satisfied, such as that the air-fuel ratio sensor 32 and the three way catalyst 34 are in an active state, during operation of the internal combustion engine 10.

[Air-Fuel Ratio Detection for Each Cylinder According to First Embodiment]

(Relationship Between Ratio of Specific Heats of Burned Gas and in-Cylinder Air-Fuel Ratio)

FIG. 2 is a graph showing a relationship between the ratio ($\kappa$) of specific heats of a burned gas and the air-fuel ratio (A/F) noted in the first embodiment of the present invention. FIG. 3 is a graph showing a relationship between the ratio of specific heats and the gas temperature. The relationship shown in FIG. 3 is an example for air and a combustion gas at the stoichiometric air-fuel ratio (excess air ratio $\lambda=1$) from a hydrocarbon fuel ($C_nH_{2n}$) that does not show exactly the same tendency as gasoline as the fuel for the internal combustion engine 10 but shows a tendency similar to that of gasoline.

As shown in FIG. 2, the burned gas in the cylinder (in-cylinder gas in an expansion stroke after a combustion end point) has a property that the ratio of specific heats of the burned gas is lowest at the stoichiometric air-fuel ratio and increases as the in-cylinder air-fuel ratio becomes richer or leaner than the stoichiometric air-fuel ratio. This property is derived two factors described below.

A first factor is the composition of the gas in the cylinder. When a hydrocarbon fuel, such as gasoline, is burned, $CO_2$, $H_2O$, $CO$, $H_2$ and the like is formed. These molecules are all diatomic molecules or triatomic molecules. The ratio of specific heats of the diatomic molecules is approximately 1.4 at 0° C., and the ratio of specific heats of the triatomic molecules is approximately 1.3 to 1.33 at 0° C. That is, the ratio of specific heats of the triatomic molecule is lower than that of the diatomic molecule. Thus, the ratio of specific heats decreases as the proportion of the triatomic molecules in the burned gas increases, and increases as the proportion of the diatomic molecules in the burned gas increases. At the stoichiometric air-fuel ratio, the fuel reacts with just the right amount of oxygen during combustion, so that the proportion of $CO_2$ and $H_2O$, which are triatomic molecules, is highest, and accordingly the ratio of specific heats is lowest. At an air-fuel ratio richer than the stoichiometric air-fuel ratio, the proportion of $CO$ and $H_2$, which are diatomic molecules, is higher than that at the stoichiometric air-fuel ratio, and the richer the air-fuel ratio is, the higher the proportion of $CO$ and $H_2$ is. At an air-fuel ratio leaner than the stoichiometric air-fuel ratio, the proportion of $O_2$, which is a diatomic molecule, is higher than that at the stoichiometric air-fuel ratio, and the leaner the air-fuel ratio is, the higher the proportion of $O_2$ is. Thus, the ratio of specific heats increases as the air-fuel ratio becomes richer or leaner than the stoichiometric air-fuel ratio. As can be seen from the above description, from the viewpoint of the influence of the gas composition, the ratio of specific heats of the burned gas is lowest at the stoichiometric air-fuel ratio and increases as the air-fuel ratio becomes richer or leaner than the stoichiometric air-fuel ratio, as shown by the thin solid line in FIG. 2.

A second factor is the temperature of the gas in the cylinder. Given the same amount of air, the ratio (amount of combustion gas/amount of heat release) of the amount of heat release of the fuel to the amount of the combustion gas (the sum of the amounts of the air and the fuel that contribute to the combustion) is lowest at the stoichiometric air-fuel ratio and increases as the air-fuel ratio becomes richer or leaner than the stoichiometric air-fuel ratio. Thus, the temperature of the burned gas decreases as the air-fuel ratio becomes richer or leaner than the stoichiometric air-fuel ratio. To be more specific, as the air-fuel ratio becomes richer than the stoichiometric air-fuel ratio, the amount of heat release does not substantially change compared with that at the stoichiometric air-fuel ratio, while the amount of the combustion gas increases due to the increase of the amount of the fuel. On the other hand, as the air-fuel ratio becomes leaner than the stoichiometric air-fuel ratio, the decrease of the amount of heat release due to the decrease of the amount of the fuel has a greater influence on the gas temperature than the decrease of the amount of the combustion gas due to the decrease of the amount of the fuel. In addition, as shown in FIG. 3, the ratio of specific heats increases as the gas temperature decreases. As can be seen from the above description, not only the gas composition but also the gas temperature serves to make more noticeable the property of the burned gas that the ratio of specific heats is lowest at the stoichiometric air-fuel ratio and increases as the air-fuel ratio becomes richer or leaner than the stoichiometric air-fuel ratio, as shown by the thick solid line in FIG. 2.

(Calculation of Polytropic Index in Expansion Stroke)

If the ratio of specific heats of the burned gas can be calculated from the output value of the in-cylinder pressure sensor 30, the air-fuel ratio can be grasped according to the relationship shown in FIG. 2. However, the actual burned gas is not the ideal gas, the expansion stroke is not an adiabatic process because of the cooling loss, and a cylinder compression leak can occur. It is therefore difficult to estimate the ratio of specific heats itself of the burned gas from the output value of the in-cylinder pressure sensor 30. However, the expansion stroke can be treated as a polytropic change that considers heat exchange with the outside.

FIG. 4 is a log-log P-V graph for the compression stroke and the expansion stroke of the internal combustion engine 10. For the polytropic change in the expansion stroke, it can be considered that a relational expression ($PV^m$=constant) holds, where "m" denotes the polytropic index. On the log-log graph, the relationship between the in-cylinder pressure P and the in-cylinder volume V in the expansion stroke is represented as a straight line having a slope of −m. In the expansion stroke after completion of the combustion period (specifically, after the combustion end point and before opening of the exhaust valve 22), the polytropic index m assumes a value equivalent to the ratio of specific heats of the burned gas in the actual engine (more specifically, a value satisfactorily close to the ratio of specific heats of the burned gas selected from among combustion parameters that can be calculated from the output value of the in-cylinder pressure sensor 30).

The polytropic index m in the expansion stroke can be calculated according to the formula (1) below using the above relational expression and the in-cylinder pressure P and the in-cylinder volume V at arbitrary two points (points A and B in FIG. 4) in the expansion stroke after the combustion end point and before the opening timing of the exhaust valve 22, provided that the polytropic index m is constant between the two points. The polytropic index m is not exclusively calculated by using two points in the expansion stroke after the combustion end point and before the opening timing of the exhaust valve 22 but can be statistically calculated from the in-cylinder pressure P and the in-cylinder volume V at two or more points in the expansion stroke.

[Math. 1]

$$m = \log_{\left(\frac{V_B}{V_A}\right)}\left(\frac{P_A}{P_B}\right) \qquad (1)$$

(Method of Detecting in-Cylinder Air-Fuel Ratio)

Since the polytropic index m in the expansion stroke after completion of the combustion period assumes a value close to the ratio of specific heats of the burned gas, it can be considered that a relationship similar to the relationship between the ratio of specific heats and the air-fuel ratio described above with reference to FIG. 2 holds between the polytropic index in and the in-cylinder air-fuel ratio (see FIG. 7B described later). Since the polytropic index m can be calculated on the actual machine from the output of the in-cylinder pressure sensor 30 according to the formula (1), it can be said that the in-cylinder air-fuel ratio can be grasped if the relationship between the polytropic index m and the air-fuel ratio is known. However, the ratio of specific heats and the polytropic index m are not uniquely determined by their relationships with the in-cylinder air-fuel ratio. This is because the ratio of specific heats and the polytropic index m are influenced by the in-cylinder gas temperature, which changes due to a change of the cooling loss, which occurs when the values of the operational condition parameters of the internal combustion engine 10, such as the engine speed and the temperature of the engine cooling water, change. Primary operational condition parameters involved with the cooling loss include the ignition timing, the EGR rate and the engine load factor, in addition to the engine speed and the temperature of the engine cooling water.

FIG. 5A and FIG. 5B are graphs for illustrating a relationship between the change of the temperature of the gas in the cylinder and the change of the polytropic index in in the expansion stroke. Using the engine speed as an example of the operational condition parameters described above, FIG. 5A and FIG. 5B show how the temperature of the gas in the cylinder and the polytropic index m change as the engine speed increases and decreases.

As shown in FIG. 5B, the temperature of the gas in the cylinder (the temperature of the burned gas) is highest in the vicinity of the stoichiometric air-fuel ratio and decreases as the air-fuel ratio becomes richer or leaner than the stoichiometric air-fuel ratio. Besides, at each air-fuel ratio, the gas temperature increases as the engine speed increases. A difference in engine speed leads to a difference in gas temperature, which leads to a difference in ratio of specific heats, which leads to a corresponding difference in polytropic index m in the expansion stroke. More specifically, as shown in FIG. 5A, at each air-fuel ratio, the polytropic index m is smaller when the engine speed is high than when the engine speed is low.

It can be said from the above description that, for an operational condition parameter involved with the cooling loss, such as the engine speed, if the polytropic index m is corrected according to the difference of the in-cylinder gas temperature due to the difference of the value of the operational condition parameter under the current operational condition with respect to the value of the operational condition parameter under a certain operational condition, the relationship between the polytropic index m in the expansion stroke and the in-cylinder air-fuel ratio can be evaluated without being affected by the difference of the value of the operational parameter related to the correction.

In view of this, according to this embodiment, relationship information that prescribes the relationship between the polytropic index m in the expansion stroke and the in-cylinder air-fuel ratio under a reference operational condition (the V-shaped curve shown in FIG. 7B described later, referred to as an "m-A/F curve" hereinafter) is stored in the ECU 40 as a map. More specifically, the relationship information (the m-A/F curve) referred to herein is a curve that prescribes the relationship between the polytropic index m in the expansion stroke and the in-cylinder air-fuel ratio in an X-Y plane with the X axis indicating the in-cylinder air-fuel ratio and the Y axis indicating the polytropic index m in the expansion stroke. The reference operational condition referred to herein is an operational condition under which each operational condition parameter involved with the cooling loss assumes an arbitrary reference value.

In addition, the polytropic index m in the expansion stroke calculated from the output of the in-cylinder pressure sensor 30 is corrected based on the various operational condition parameters described above. More specifically, the polytropic index m calculated from the output of the in-cylinder pressure sensor 30 is corrected by the difference in polytropic index m caused by the difference of the value of an operational condition parameter under the current operational condition with respect to the value of the operational condition parameter under the reference operational condition. Furthermore, the in-cylinder air-fuel ratio is calculated based on the corrected polytropic index m in the expansion stroke, the result of determination of whether the cylinder for which the air-fuel ratio is detected is a rich cylinder or a lean cylinder, and the m-A/F curve under the reference operational condition.

(Specific Process According to First Embodiment)

FIG. 6 is a flowchart showing a routine performed by the ECU 40 to implement a method of detecting the air-fuel ratio in each cylinder according to the first embodiment of the present invention. This routine is activated when a predetermined execution condition for detecting the air-fuel ratio in each cylinder is satisfied. In this example, the execution condition is satisfied in a steady operation where the air-fuel ratio of the exhaust gas flowing to the three way catalyst 34 under the air-fuel ratio feedback control (that is, the air-fuel ratio of the confluent exhaust gas of the exhaust gas from all the cylinders) is controlled to be the stoichiometric air-fuel ratio. However, this detection method can be performed even if the internal combustion engine 10 is not strictly in the steady state, unless a significant fluctuation that affects the detection process is found in the air-fuel ratio or the intake air amount. In this example, this routine is performed for all the cylinders.

In the routine shown in FIG. 6, in Step 100, the ECU 40 stores in-cylinder pressure data (that is, in-cylinder pressure history) for each cylinder (all the cylinders) over successive cycles in synchronization with the crank angle in one cycle based on the detection values from the in-cylinder pressure sensor (CPS) 30.

The ECU 40 then proceeds to Step 102 and calculates a maximum amount of heat release Qmax for each cylinder based on the in-cylinder pressure history stored. The amount of heat release Q for the in-cylinder pressure P and the in-cylinder volume V at any crank angle can be calculated according to the formula (2) below, and therefore, the maximum amount of heat release Qmax can be calculated as the maximum value of the amount of heat release Q calculated. The data calculation period in which the amount of heat release Q is calculated in synchronization with the crank angle ends at the opening timing of the exhaust valve 22, which is detected by the exhaust cam angle sensor 46. In the formula (2), $P_0$ and $V_0$ denote the in-cylinder pressure and the in-cylinder volume at a calculation start point $\theta_0$ (a predetermined crank angle in the compression stroke that is determined with a margin with respect to possible combustion start points).

[Math. 2]

$$Q = \int PdV + \frac{1}{\kappa - 1}(PV - P_0V_0) \quad (2)$$

The ECU 40 then proceeds to Step 104 and determines whether each cylinder of the internal combustion engine 10 is a rich cylinder or a lean cylinder based on the value of the maximum amount of heat release Qmax in each cylinder. FIG. 7A and FIG. 7B are graphs for illustrating a specific example of the method of detecting the air-fuel ratio according to the first embodiment of the present invention, and the processings in Step 104 and the following steps will be described with reference to the specific example shown in FIGS. 7A and 7B. More specifically, FIG. 7A shows a relationship between the calculated value of the maximum amount of heat release Qmax and the in-cylinder air-fuel ratio under a certain operational condition, and FIG. 7B shows a relationship between the polytropic index m and the in-cylinder air-fuel ratio (that is, the m-A/F curve) under the reference operational condition described above.

In this Step 104, a cylinder is determined to be a rich cylinder that has an air-fuel ratio richer than the stoichiometric air-fuel ratio if the maximum amount of heat release Qmax calculated for the cylinder is greater than a predetermined value, and is determined to be a lean cylinder that has an air-fuel ratio leaner than the stoichiometric air-fuel ratio if the maximum amount of heat release Qmax calculated for the cylinder is equal to or smaller than the predetermined value. The predetermined value of the maximum amount of heat release Qmax referred to herein is a threshold of the maximum amount of heat release Qmax that is previously set for the operational condition and serves as a criterion for determining whether the detection target cylinder is a rich cylinder or a lean cylinder by considering the relationship between the maximum amount of heat release Qmax having the tendency shown in FIG. 7A and the air-fuel ratio.

The ECU 40 then proceeds to Step 106 and calculates, according to the formula (1), the polytropic index m in the expansion stroke for each cylinder from in-cylinder pressures $P_A$ and $P_B$ and in-cylinder volumes $V_A$ and $V_B$ at two points that are determined from the output of the in-cylinder pressure sensor 30 in the expansion stroke at or after the combustion end point (the crank angle at which the maximum amount of heat release Qmax is achieved) and before the opening of the exhaust valve 22.

The ECU 40 the proceeds to Step 108 and corrects the polytropic index m calculated in Step 106 based on an operational condition parameter involved with the cooling loss. In this Step 108, the polytropic index m is corrected based on the engine speed, the temperature of the engine cooling water, the ignition timing, the EGR rate and the engine load factor. However, the correction of the polytropic index m according to the present invention may be made based on one or some of these operational condition parameters, rather than on all of these operational condition parameters. Furthermore, if there is any operational condition parameter involved with the cooling loss other than the operational condition parameters listed above, the other operational condition parameter may be used in addition to or as an alternative to the operational condition parameters described above. Possible operational condition parameters other than the operational condition parameters described above include the compression ratio of an internal combustion engine whose compression ratio is variable.

In this Step 108, the polytropic index m calculated in Step 106 is corrected by adding various polytropic index correction amounts described below to the polytropic index m. FIG. 8A to FIG. 8E are graphs showing settings of various polytropic index correction amounts used in the processing of Step 108. In the FIG. 8A to FIG. 8E, a polytropic index correction amount for the engine speed is set to decrease as the engine speed increases in consideration of how the polytropic index m changes as the cooling loss changes as a result of a change in the engine speed. Similarly, the correction amount for the temperature of the engine cooling water is set to decrease as the temperature of the engine cooling water increases, the correction amount for the ignition timing is set to decrease as the ignition timing is retarded (with respect to an optimal ignition timing (MBT), for example), the correction amount for the EGR rate is set to decrease as the EGR rate increases, and the correction amount for the engine load factor is set to decrease as the engine load factor increases. In addition, as shown in FIG. 8A to FIG. 8E, each polytropic index correction amount is set so that the value thereof under the reference operational condition (that is, the reference value described above) is zero. According to the correction using these polytropic index correction amounts, the polytropic index m calculated from the output of the in-cylinder pressure sensor 30 can be corrected to be smaller as the engine speed becomes higher, as the temperature of the engine cooling water becomes higher, as the ignition timing becomes more significantly retarded, as the EGR rate becomes higher and as the engine load factor becomes higher.

The ECU 40 then proceeds to Step 110. In Step 110, the ECU 40 refers to the result of the determination in Step 104 and proceeds to Step 112 if the cylinder for which the air-fuel ratio is to be detected is a rich cylinder, and proceeds to Step 114 if the cylinder for which the air-fuel ratio is to be detected is a lean cylinder. In Step 112, as shown in FIG. 7B, the polytropic index m corrected is converted into an air-fuel ratio according to a part of the m-A/F curve under the reference operational condition on the richer side than the stoichiometric air-fuel ratio. More specifically, the air-fuel ratio at the intersection between the part of the m-A/F curve on the richer side and the polytropic index m corrected (shown by a circle) is calculated as the value of the air-fuel ratio of the cylinder for which the air-fuel ratio is to be detected. The processing of Step 114 is similar to the processing of Step 112, and the polytropic index m corrected is converted into an air-fuel ratio according to a part of the m-A/F curve under the reference operational condition on the leaner side than the stoichiometric air-fuel ratio.

According to the routine shown in FIG. 6 described above, the in-cylinder air-fuel ratio is calculated based on the corrected polytropic index m in the expansion stroke, the result of the determination of whether the cylinder for which the air-fuel ratio is to be detected is a rich cylinder or a lean cylinder, and the m-A/F curve under the reference operational condition. The relationship between the polytropic index m and the air-fuel ratio noted in this embodiment shows a tendency of the polytropic index m to be lowest at the stoichiometric air-fuel ratio and to increase as the air-fuel ratio becomes richer or leaner than the stoichiometric air-fuel ratio. Thus, the same polytropic index m may be attained at different values of the air-fuel ratio. Under the situation where the air-fuel ratio can vary to be richer or leaner than the stoichiometric air-fuel ratio, such as the situation supposed in this embodiment, it is required to determine whether the cylinder for which the air-fuel ratio is to be detected is a rich cylinder or a lean cylinder. In addition, in the correction of the polytropic index m described above, the influence, on the polytropic index m, of the operational condition parameters involved with the cooling loss (that is, the influence, on the polytropic index m, of the temperature of the gas in the cylinder due to the factors other than the air-fuel ratio) can be excluded, and the change of the gas temperature caused solely by the change of the air-fuel ratio can be left as the influence of the gas temperature on the polytropic index m. As a result, the in-cylinder air-fuel ratio can be detected based on the information on the polytropic index m in the expansion stroke calculated from the output of the in-cylinder pressure sensor 30 including the polytropic index in the region where the air-fuel ratio is richer than the stoichiometric air-fuel ratio (that is, the information on the state of the burned gas itself).

As described below with reference to FIG. 9, the air-fuel ratio of each cylinder calculated with the method according to the first embodiment described above may be used to detect an air-fuel ratio imbalance between the cylinders. FIG. 9 is a flowchart showing a routine performed by the ECU 40 to implement such a process of detecting an air-fuel ratio imbalance between the cylinders.

In the routine shown in FIG. 9, in Step 200, the ECU 40 obtains the air-fuel ratio of each cylinder calculated with the routine shown in FIG. 6. The ECU 40 then proceeds to Step 202 and calculates a relative difference in air-fuel ratio between the cylinders. The relative difference in air-fuel ratio between the cylinders may be the relative difference between two cylinders for which the difference is the maximum.

The ECU 40 then proceeds to Step 204 and determines whether or not the difference in air-fuel ratio between the cylinders calculated in Step 202 described above is greater than a predetermined criterion value. The criterion value used in this Step 204 is a preset threshold for determining whether the calculated difference in air-fuel ratio between the cylinders indicates a level of air-fuel ratio imbalance that is required to be detected in the internal combustion engine 10. If the result of the determination in this Step 204 is affirmative, the ECU 40 proceeds to Step 206 and determines that there is a significant level of air-fuel ratio imbalance that should be detected between the cylinders.

In the first embodiment described above, whether each cylinder is a rich cylinder or a lean cylinder is determined based on the maximum amount of heat release Qmax calculated from the in-cylinder pressure detected by the in-cylinder pressure sensor 30. However, the combustion parameter calculated from the in-cylinder pressure detected by the in-cylinder pressure sensor 30 and used for the rich/lean determination is not limited to the amount of heat release Q but may be the burning velocity, for example. For example, the burning velocity can be calculated based on the main combustion period (10 to 90% combustion period) that can be determined from the mass fraction burned (MFB), and the shorter the main combustion period is, the higher the burning velocity is. The MFB at an arbitrary crank angle $\theta$ can be calculated from the data on the amount of heat release Q synchronized with the crank angle according to the formula (3) below. Thus, the crank angle at which the MFB reaches a predetermined value can be determined according to the formula (3). In the formula (3), $\theta_{sta}$ denotes a combustion start point, and $\theta_{fin}$ denotes a combustion end point.

[Math. 3]

$$MFB = \frac{Q(\theta) - Q(\theta_{Sta})}{Q(\theta_{fin}) - Q(\theta_{sta})} \quad (3)$$

FIG. 10 is a graph showing a relationship between the burning velocity and the in-cylinder air-fuel ratio. As shown in FIG. 10, as with the amount of heat release Q (the maximum amount of heat release Qmax shown in FIG. 7A), the burning velocity is highly sensitive to the air-fuel ratio in the region leaner than the stoichiometric air-fuel ratio. However, in the region richer than the stoichiometric air-fuel ratio, the burning velocity is less sensitive to the air-fuel ratio because of the characteristics of the laminar burning velocity. Thus, the burning velocity may be used instead of the amount of heat release Q (maximum amount of heat release Qmax) used in the first embodiment described above. More specifically, the cylinder for which the air-fuel ratio is to be detected may be determined to be a rich cylinder if the burning velocity is higher than a predetermined value.

Whether each cylinder is a rich cylinder or a lean cylinder is not necessarily determined by using the combustion parameter based on the in-cylinder pressure detected by the in-cylinder pressure sensor 30. For example, the method of determining whether each cylinder is a rich cylinder or a lean cylinder may involve using the air-fuel ratio sensor 32 and estimating whether the air-fuel ratio of each cylinder is richer or leaner than the stoichiometric air-fuel ratio by considering the time required for the exhaust gas from the cylinder to reach the air-fuel ratio sensor 32.

In the first embodiment described above, the m-A/F curve that prescribes the relationship between the polytropic index m in the expansion stroke and the air-fuel ratio is used to calculate the air-fuel ratio. However, the index value of the air-fuel ratio (the value shown on the horizontal axis of the graphs shown in FIG. 7B showing the m-A/F curve) used along with the polytropic index in the expansion stroke to prescribe the relationship information according to the present invention is not limited to the air-fuel ratio itself (that is, the weight ratio between the air amount and the fuel amount) but can be any index value correlated to the air-fuel ratio, such as the excess air ratio or the equivalence ratio.

In the first embodiment described above, the internal combustion engine 10 that uses gasoline, which is one of hydrocarbon fuels, as the fuel has been described, for example. However, the fuel used in the present invention is not limited to the hydrocarbon fuels, such as gasoline, but may be any fuel that produces a burned gas in which each proportion of the diatomic molecule and the triatomic molecule in the burned gas changes with the air-fuel ratio in the manner described above in the first embodiment, such as a hydrogen fuel.

in the first embodiment described above, the detection of the air-fuel ratio is performed for all the cylinders of the internal combustion engine 10, for example. However, the detection of the in-cylinder air-fuel ratio and the detection of the air-fuel ratio imbalance between the cylinders according to the present invention are not necessarily performed for all the cylinders but may be performed for a group of cylinders to be evaluated that includes some of the cylinders of the multi-cylinder internal combustion engine. More specifically, for example, in an example where a group of cylinders that share one exhaust gas purifying catalyst (the three way catalyst, for example) does not include all the cylinders but include some of the cylinders, the group of cylinders that share the exhaust gas purifying catalyst may be the group of cylinders to be evaluated. This holds true for an example where an exhaust gas purifying catalyst is provided for each bank in a V-engine or an example where an exhaust gas purifying catalyst is provided for each group of cylinders in which explosion occurs at regular or substantially regular intervals in an in-line engine.

In the first embodiment described above, the "in-cylinder pressure detecting means" according to the first aspect of the present invention described above is implemented by the ECU 40 performing the processing of Step 100 described above, the "cylinder air-fuel ratio determining means" according to the first aspect of the present invention described above is implemented by the ECU 40 performing the processing of Step 104 described above, the "polytropic index calculating means" according to the first aspect of the present invention described above is implemented by the ECU 40 performing the processing of Steps 106 and 108 described above, and the "air-fuel ratio calculating means" according to the first aspect of the present invention described above is implemented by the ECU 40 performing the processing of Steps 110 to 114 described above.

In the first embodiment described above, the "imbalance detecting means" according to the sixth aspect of the present invention described above is implemented by the ECU 40 performing the series of processing of the routine shown in FIG. 9 described above.

DESCRIPTION OF SYMBOLS 10 internal combustion engine
12 piston
14 combustion chamber
16 intake channel
18 exhaust channel
20 intake valve
22 exhaust valve
24 throttle valve
26 fuel injection valve
28 spark plug
30 in-cylinder pressure sensor
32 air-fuel ratio sensor
34 three way catalyst
36 EGR channel
38 EGR valve
40 Electronic Control Unit (ECU)
42 crank angle sensor
44 air flow sensor
46 exhaust cam angle sensor

The invention claimed is:

1. An air-fuel ratio detection device for an internal combustion engine including one or more cylinders and each cylinder including a fuel injection valve to directly inject a fuel into the cylinder, the air-fuel ratio detection device comprising:
 an in-cylinder pressure detector configured to detect an in-cylinder pressure; and
 an ECU, the ECU programmed to:
  (a) determine whether a cylinder for which an index value of an in-cylinder air-fuel ratio is to be calculated is a rich cylinder, for which the in-cylinder air-fuel ratio is richer than a stoichiometric air-fuel ratio, or a lean cylinder, for which the in-cylinder air-fuel ratio is leaner than the stoichiometric air-fuel ratio;
(b) calculate a polytropic index in an expansion stroke from the in-cylinder pressure detected by the in-cylinder pressure detector;
(c) correct the calculated polytropic index based on an operational condition parameter of the internal combustion engine; and
(d) calculate the index value of the in-cylinder air-fuel ratio based on the corrected polytropic index in the expansion stroke, a result of the determination of whether the cylinder for which the index value of the in-cylinder air-fuel ratio is to be calculated is a rich cylinder or a lean cylinder, and relationship information that prescribes a relationship between the polytropic index in the expansion stroke and the index value of the in-cylinder air-fuel ratio under a reference operational condition;
wherein said ECU is further programmed to control the fuel injection valve in each cylinder, based on the index value of the in-cylinder air-fuel ratio, to adjust a fuel injection amount for each cylinder so as to set an air-fuel ratio of exhaust gas from said one or more cylinders to a stoichiometric air-fuel ratio.

2. The air-fuel ratio detection device according to claim 1, wherein the operational condition parameter used for the correction of the polytropic index in the expansion stroke is at least one of an engine speed, a temperature of engine cooling water, an ignition timing, an EGR rate and an engine load factor.

3. The air-fuel ratio detection device according to claim 2, wherein the ECU is programmed to correct the polytropic index in the expansion stroke so as to be smaller as the engine speed is higher, as the temperature of the engine cooling water is higher, as the ignition timing is retarded, as the EGR rate is higher, or as the engine load factor is higher.

4. The air-fuel ratio detection device according to claim 1, wherein the ECU is programmed to calculate an amount of heat release or a burning velocity from the in-cylinder pressure detected by the in-cylinder pressure-detector and determines that the cylinder for which the index value of the in-cylinder air-fuel ratio is to be calculated is a rich cylinder when the calculated amount of heat release or burning velocity is greater than a predetermined value.

5. The air-fuel ratio detection device according to claim 1, wherein the ECU is programmed to calculate the polytropic index in the expansion stroke from in-cylinder pressures and in-cylinder volumes at two or more points in the expansion stroke at or after a combustion end point and before an opening timing of an exhaust valve.

6. The air-fuel ratio detection device according to claim 1, wherein the internal combustion engine includes a plurality of cylinders,
wherein the in-cylinder pressure detector is configured to detect an in-cylinder pressure of each of the plurality of cylinders, and
wherein the ECU is programmed to determine that the air-fuel ratio is imbalance between cylinders when a difference in air-fuel ratio between the cylinders based on the calculated index value of the in-cylinder air-fuel ratio is greater than a predetermined criterion value.

7. The air-fuel ratio detection device according to claim 1, wherein the reference operational condition is an operational condition where the operational condition parameter equals an arbitrary reference value.

8. The air-fuel ratio detection device according to claim 1, wherein the relationship information is a curve that prescribes a relationship between the polytropic index in the expansion stroke and the index value of the in-cylinder air-fuel ratio in an X-Y plane with an X axis indicating the index value of the in-cylinder air-fuel ratio and a Y axis indicating the polytropic index in the expansion stroke.

* * * * *